(12) United States Patent
Belanoff

(10) Patent No.: US 8,450,379 B2
(45) Date of Patent: May 28, 2013

(54) METHODS FOR TREATING MIGRAINE

(75) Inventor: Joseph K. Belanoff, Woodside, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 1041 days.

(21) Appl. No.: 10/703,069

(22) Filed: Nov. 5, 2003

(65) Prior Publication Data

US 2004/0132703 A1 Jul. 8, 2004

Related U.S. Application Data

(60) Provisional application No. 60/424,199, filed on Nov. 5, 2002.

(51) Int. Cl.
*A61K 31/045* (2006.01)
*A61K 31/05* (2006.01)

(52) U.S. Cl.
USPC .......... 514/729; 514/724; 514/730; 514/731; 514/732; 514/733

(58) Field of Classification Search
USPC ................................. 514/179, 729–733, 724
See application file for complete search history.

(56) References Cited

U.S. PATENT DOCUMENTS

| | | | | |
|---|---|---|---|---|
| 5,250,529 A | * | 10/1993 | Theoharides | ............ 514/254.07 |
| 5,468,741 A | | 11/1995 | Yen | |
| 5,521,166 A | * | 5/1996 | Grubb | ............................ 514/170 |
| 6,166,013 A | * | 12/2000 | Coghlan et al. | ............ 514/239.5 |
| 6,380,223 B1 | * | 4/2002 | Dow et al. | ...................... 514/357 |
| 6,579,898 B2 | | 6/2003 | Humphrey | |
| 6,589,947 B1 | * | 7/2003 | Hamanaka et al. | ........... 514/183 |
| 2003/0148987 A1 | * | 8/2003 | Morris et al. | ................... 514/44 |

FOREIGN PATENT DOCUMENTS

WO WO 98/03179 A 1/1998

OTHER PUBLICATIONS

Hardman et al. "The pharmaceutical Basis of Therapeutics," 1996, pp. 1430-1431.*
Morgan et al. "Dscovery of potent, nonsteroidal, and highly selective glucocorticoid receptor antagonists," J. Med. Chem. Jun. 2002, vol. 45, No. 12, pp. 2417-2424.*
The Merck Manual, fifteenth edition, 1987, pp. 1355-1356.*
Kettel, L.M. et al; "Endocrine Responses to Long-Term Administration of the Antiprogesterone TU-486 in Patients with Pelvic Endometriosis"; *Fertility and Sterility*; 1991; pp. 402-407; vol. 56, No. 3; (Abstract from database BIOSIS on ACS; Accession No. 1991:505867).
Adelman, J., et al., "Current options for the prevention and treatment of migraine," *Clinical Therapeutics*, vol. 23(6): 772-788 (Jun. 2001).
Agarwal, M.K., "The antiglucocorticoid action of mifepristone," *Pharmacology and Therapeutics*, vol. 70(3): 183-213 (1996).
Sicuteri, F., et al.., "Naloxone effectiveness on spontaneous and induced perspective disorders in migraine," *Headache*, vol. 23(4): 179-183 (1983).

* cited by examiner

*Primary Examiner* — Shengjun Wang
(74) *Attorney, Agent, or Firm* — Kilpatrick Townsend & Stockton

(57) ABSTRACT

This invention relates to the discovery that agents capable of inhibiting the biological action of the glucocorticoid receptor can be used in methods for treating migraine in a subject.

8 Claims, No Drawings

METHODS FOR TREATING MIGRAINE

CROSS REFERENCES TO RELATED APPLICATIONS

This application claims priority to U.S. 60/424,199, filed Nov. 5, 2002, which is incorporated herein by reference in its entirety.

FIELD OF THE INVENTION

This invention relates to the discovery that agents capable of inhibiting the biological action of the glucocorticoid receptor can be used in methods for reducing, eliminating, or preventing migraine in a subject.

BACKGROUND OF THE INVENTION

Migraine is a common, underdiagnosed, and undertreated neurological disorder. Although migraine is the most common cause of severe, recurring headache, headache is only one of them any ways the disease manifests itself. Migraine may also include visual disturbances, alterations in consciousness, photophobia, or phonophobia. The condition can be truly debilitating and the pain can interfere with a person's ability to live a normal productive life. Indeed, attacks can force the sufferer to abandon everyday activities for up to 3 day. Even in symptom-free period, sufferers may live in fear of the next attack.

More than 23 million Americans older than 12 years of age experience migraine, with a 17.6% prevalence in females and 5.7% in males. Given the high prevalence of sufferers, it is not surprising that American businesses lose upwards of 50 billion dollars annually because of absenteeism, reduced worker productivity, and medical expenses secondary to migraine. Thus, the economic and social consequences of migraine are enormous.

Of the different types of migraines, classical migraine (migraine with aura) and common migraine (migraine without aura) are the two most prevalent. Although migraine is caused by intermittent brain dysfunction, the precise pathophysiological mechanisms involved are not understood.

Drugs that have been used in an attempt to treat migraine include: ergotamine and ergotamine-like agents; serotonin agonists; and caffeine with ergots or other pharmacologic agents (see e.g., Silberstein, S. D., Curr. Opinion Neurology 7:258-263 (1994); Welch, K. M. A., New Engl J. Med. 329: 1476-1483 (1993); Dumar, K. L., J. Gen. Int. Med. 9:339-348 (1994); Saadah, H., Headache 32:95-97 (1992); and Becker, Arzneimittelforshung (42(4):552-555 (1992)). All of these drugs are thought to initially relieve migraine-associated pain by causing vasoconstriction. Unfortunately, this leads to numerous side effects such as chest pain or pressure, flushing, generalized tingling sensations, nausea, vomiting, pain in the legs and arms, asthenia, drowsiness, and dizziness. Acute ergotism is a particularly pernicious side effect of ergot drugs and is characterized by severe central and peripheral vasoconstriction, nausea, vomiting, diarrhea, colic, headache, vertigo, paresthesia, and possibly convulsive seizures.

Patients have, on occasion, found total or partial relief for some forms of migraine through the use of non-prescription analgesics. As outlined by Welch (New Engl J. Med. 329: 1476-1483 (1993)), the initial dosages of such analgesics are typically: aspirin, 500-650 mg; acetaminophen, 500 mg; naproxen sodium, 750-825 mg; tolfenamic acid, 200-400 mg; and, ibuprofen 200 mg. However, the absorption of these and other agents during a migraine attack has been shown to be impaired, apparently due to gastric stasis.

While significant advances have been made in dealing with migraine, none has proven to be broadly effective for an extended time frame, since the side effects associated with the various options limits their value.

Clearly, there is a need in the art for an effective migraine treatment. Ideally a migraine drug formulation should be nonaddictive and free of vasoactive agents. This requires the exclusion of ergots, serotonin agonists such as sumatriptan, and caffeine. The formulation should relieve or eliminate migraine symptoms, and should be effective when used for acute treatment or when used prophylactically. The invention disclosed herein meets these and other needs. The current invention is based, at least in part, on the surprising discovery that glucocorticoid receptor antagonists are effective agents for the treatment of migraine.

Corticosteroids are steroid hormones released by the adrenal glands. The most significant human adrenal corticosteroids are cortisol, corticosterone and aldosterone. Corticosteroids produce cellular effects following binding to receptors located in the cytoplasm of the cell. Two general classes of corticosteroid receptors are now recognized, the mineralocorticoid receptors (also termed type I, or MR) and the glucocorticoid receptors (also termed type II, or GR).

Mineralocorticoid receptors (MRs) bind cortisol with tenfold higher affinity than glucocorticoid receptors (GRs) bind glucocorticoids. Thus, the activation of the two classes of receptors may differ depending on the corticosteroid (cortisol) concentration. Blood levels of the glucocorticoid cortisol vary over a wide range during the day. In general, normal cortisol concentrations in the blood range from about 0.5 nM to about 50 nM; however, in response to stress, cortisol concentration may exceed 100 nM.

Glucocorticoid blockers are agents that block or reduce the effects of glucocorticoids. Such interference with glucocorticoid action may, for example, be due to interference with binding of glucocorticoid agonists to glucocorticoid receptors (GR), or to interference with the action of agonist-bound GR at the cell nucleus, or to interference with expression or processing of gene products induced by the action of agonist-bound GR at the nucleus. Glucocorticoid receptor antagonists (GR antagonists) are compounds which inhibit the effect of the native ligand or of glucocorticoid agonists on GR. One mode of action of GR antagonists is to inhibit the binding of GR ligands to GR. A discussion of glucocorticoid antagonists may be found in Agarwal et al. "Glucocorticoid antagonists", FEBS Lett., 217:221-226 (1987). An example of a GR antagonist is mifepristone, (11β,17β) 11[4 (dimethylamino) phenyl]-17 hydroxy-17 (1 propynyl)estra-4,9 dien-3 one, also known as RU-486 or RU-38486. See U.S. Pat. No. 4,368, 085. Mifepristone binds specifically to GR with an affinity about 18 times that of the affinity of cortisol for GR. GR antagonists may be steroids, such as mifepristone, or non-steroids.

The present inventors have determined for the first time that glucocorticoid receptor antagonists are effective agents for the treatment of migraine. Thus, the present invention fulfills the need for an effective method for the treatment of migraine by providing methods of administering glucocorticoid receptor antagonists to a subject.

BRIEF SUMMARY OF THE INVENTION

The present invention is based at least in part, upon the discovery that administration of a glucocorticoid receptor antagonist provides an effective and of improved treatment of migraine. Thus, in one aspect, the invention is directed toward methods of treating migraine in a subject, provided that the subject is not otherwise in need of treatment with a glucocorticoid receptor antagonist, and provided that the subject is not also being treated with triptans nor any other pharmaceutically prescribed entity that is predominantly metabolized by a cytochrome P450-3A4 isoenzyme.

In one aspect of the invention, the glucocorticoid receptor antagonist comprises a steroidal skeleton with at least one phenyl-containing moiety in the 11-beta position of the steroidal skeleton. In one aspect, the phenyl-containing moiety in the 11-beta position of the steroidal skeleton is a dimethylaminophenyl moiety. In another aspect, the glucocorticoid receptor antagonist is mifepristone.

In one aspect of the present invention, the glucocorticoid receptor antagonist is selected from the group consisting of 11β-(4-dimethylaminoethoxyphenyl)-17α-propynyl-17β-hydroxy-4,9-estradien-3-one and 17β-hydroxy-17α-19-(4-methylphenyl)androsta-4,9(11)-dien-3-one. In another aspect, the glucocorticoid receptor antagonist is selected from the group consisting 4α(S)-Benzyl-2(R)-prop-1-ynyl-1,2,3,4,4α,9,10,10α(R)-octahydro-phenanthrene-2,7-diol and 4α(S)-Benzyl-2(R)-chloroethynyl-1,2,3,4,4α,9,10,10α(R)-octahydro-phenanthrene-2,7-diol.

In another one aspect, the glucocorticoid receptor antagonist is (11β,17β)-11-(1,3-benzodioxol-5-yl)-17-hydroxy-17-(1-propynyl)estra-4,9-dien-3-one.

In another aspect of the present invention, the glucocorticoid receptor antagonist is administered in a daily amount of between about 0.5 to about 35 mg per kilogram of body weight per day. In another aspect, the glucocorticoid receptor antagonist is administered in a daily amount of between about 5 to about 15 mg per kilogram of body weight per day.

In one aspect of the present invention, the administration is once per day. In yet another aspect, the mode of administration is by a transdermal application, by a nebulized suspension, or by an aerosol spray. In another aspect, the mode of administration is oral.

In another aspect the invention also provides a kit for treating migraine in a subject. The kit comprises a specific glucocorticoid receptor antagonist and an instructional material teaching the indications, dosage and schedule of administration of the glucocorticoid receptor antagonist to a patient suffering from migraine.

DETAILED DESCRIPTION OF THE INVENTION

Definitions

The term "migraine" refers to a symptom complex occurring periodically that is characterized by one or more of the following symptoms: pain in the head that may be exacerbated by movement or physical activity; nausea and/or vomiting, diarrhea, photophobia, visual disturbances including scintillating appearances of light; alterations in consciousness including seizure, syncope, and confused state; vertigo, light headedness, scalp tenderness, or paresthesia. The particular combination of symptoms and their frequency and severity are used to classify migraine into numerous subclasses (see, e.g. Headache Classification Committee of the International Headache Society: *The International Classification of Headache Disorders,* $2^{nd}$ edition. Cephalalgia 24, supplement 1, 2004; available from Blackwell Publishing, 9600 Garsington Road, Oxford OX4 2DQ, UK). Not every migraine needs to meet all migraine criteria to be classified as migraine. For example, a person may have a left-temporal throbbing headache of moderate intensity worsened by physical activity. These headache features meet migraine criteria. However, this headache may not be accompanied by nausea or hypersensitivity to light or noise and, therefore, not fulfill all the criteria for migraine. Yet, if some of this person's other headaches meet all the migraine criteria, then one can say that this headache is also a migraine.

The term "migraine attack" refers to the experience of migraine symptoms. The experience may include the early premonitory symptoms, as well as any symptoms that occur during a migraine.

The term "headache" refers to pain in various parts of the head, not confined to the area of distribution of any nerve. Many types of headaches are known. For example, the classification system published by the Headache Classification Committee of the International Headache Society (IHS) in 1988 lists more than 100 types of headache (Headache Classification Committee of the International Headache Society: *The International Classification of Headache Disorders,* $2^{nd}$ edition., supra).

The term "prophylactic" refers to an agent that acts to prevent disease, such as migraine. In one aspect, a glucocorticoid receptor antagonist of the invention is administered prophylactically to prevent the onset of migraine.

The terms "treating", "treatment", "to treat" refer to means for preventing, reducing, or eliminating migraine and or the accompanying symptoms in a subject. Treatment refers to any indicia of success in prevention, reduction, elimination, or amelioration of migraine, including any objective or subjective parameter such as abatement; remission; diminishing of symptoms, prevention, or lessening of migraine symptoms or making the condition more tolerable to the subject; making the migraine less debilitating; or improving a patient's physical or mental well-being. For example, success of treatment by methods of the invention could be measured by comparing the frequency and severity of migraine attacks in the year before treatment with anti-glucocorticoids of the invention was initiated, with the year following the initiation of treatment. The prevention, treatment or amelioration of symptoms can be based on objective or subjective parameters; including the results of a physical examination, or personal interview regarding symptom severity and quality of life, or any other appropriate means known in the art.

The term "cortisol" refers to a family of compositions also referred to as hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-β-hydroxy-11-β-(4-dimethyl-aminophenyl)-17-α-(1-propynyl)-estra-4, 9-dien-3-one), or 11-β-(4dimethylaminophenyl)-17-β-hydroxy-17-α-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11β-[p-(Dimethylamino)phenyl]-17-β-hydroxy-17-(1-propynyl)-estra-4,9-dien-3-one; 11β-(4-dimethyl-aminophenyl)-17β-hydroxy-17α-(prop-1-ynyl)-estra-4,9-dien-3-one; 17β-hydroxy-11β-(4-dimethylaminophenyl-1)-17α-(propynyl-1)-estra-4,9-diene-3-one; 17β-hydroxy-11β-(4-dimethylaminophenyl-1)-17α-(propynyl-1)-E; (11β,17β)-11-[4-dimethylamino)-phenyl]-

17-hydroxy-17-(1-propynyl)estra-4,9-dien-3-one; and 11β-[4-(N,N-dimethylamino) phenyl]-17α-(prop-1-ynyl)-D-4,9-estradiene-17β-ol-3-one.

The term "specific glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" also refers to any composition or compound which inhibits any biological response associated with the binding of a GR to an agonist. By "specific", we intend the drug to preferentially bind to the GR rather than the mineralocorticoid receptor (MR) with an affinity at least 100-fold, and frequently 1000-fold.

A subject "not otherwise in need of treatment with a glucocorticoid receptor antagonist" is an individual or patient who is not being treated with antiglucocorticoid compounds for any disorder accepted by the medical community to be effectively treatable with antiglucocorticoid compounds. Conditions known in the art and accepted by the medical community to be effectively treatable with glucocorticoid receptor antagonists include: Cushing's disease, drug withdrawal, dementia, stress disorders, anxiety disorders (U.S. Pat. No. 5,741,787), depression, psychotic major depression (U.S. Pat. No. 6,150,349), schizoaffective disorder, diabetes, rheumatoid arthritis, autoimmune disease, HIV infection, dermatitis, inflammation, fibromyalgia, central nervous system disease, neurodegeneration, neural injuries, pelvic pain, and various cancers.

A subject "not also being treated with triptans nor any other pharmaceutically prescribed entity that is predominantly metabolized by a cytochrome P450-3A4 isoenzyme" is an individual or patient who is not also being treated with triptan drugs such as elitriptan or sumatriptan for any disorder accepted by the medical community to be effectively treatable with triptan drugs. Triptan drugs are thought to act through their affect on the metabolic activity of the P450-3A4 enzyme. Thus, a subject "not also being treated with triptans nor any other pharmaceutically prescribed entity that is predominantly metabolized by a cytochrome P450-3A4 isoenzyme" is not being treated with any drugs that affect the metabolic activity of the P450-3A4 enzyme in a manner similar to the manner in which triptan drugs affect the P450-3A4 enzyme.

I. Introduction

This invention pertains to the surprising discovery that agents that can inhibit glucocorticoid-induced biological responses are effective for treating migraine. In treating migraine, the methods of the invention can ameliorate, eliminate, reduce or prevent the symptoms of migraine. In one embodiment, the methods of the invention use agents that act as GR antagonists, blocking the interaction of cortisol with GR, to treat migraine. The methods of the invention are effective in treating migraine in an afflicted patient.

Cortisol acts by binding to an intracellular, glucocorticoid receptor (GR). In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same signal transduction pathways.

The biological effects of cortisol, including pathologies or dysfunctions caused by hypercortisolemia, can be modulated and controlled at the GR level using receptor antagonists. Several different classes of agents are able to act as GR antagonists, i.e., to block the physiologic effects of GR-agonist binding (the natural agonist is cortisol). These antagonists include compositions, which, by binding to GR, block the ability of an agonist to effectively bind to and/or activate the GR. One family of known GR antagonists, mifepristone and related compounds, are effective and potent anti-glucocorticoid agents in humans (Bertagna, *J. Clin. Endocrinol. Metab.* 59:25, 1984). Mifepristone binds to the GR with high affinity, with a K of dissociation<$10^{-9}$ M (Cadepond, *Annu. Rev. Med* 48:129, 1997). Thus, in one embodiment of the invention, mifepristone and related compounds are used to treat migraine in a subject.

As the methods of the invention include use of any means to inhibit the biological effects of an agonist-bound GR, illustrative compounds and compositions which can be used to treat migraine in a subject are also set forth. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are set forth below.

II. Diagnosis of Migraine in a Subject

Migraine is diagnosed by determining whether some of a person's recurrent headaches meet migraine criteria as disclosed in *The International Classification of Headache Disorders, $2^{nd}$ edition*, Headache Classification Committee of the International Headache Society: Cephalalgia 24, supplement 1, 2004; which is incorporated herein by reference. For example, the diagnostic criteria set forth by the International Headache Society for diagnosis of migraine without aura are shown in Table 1. Migraines without aura are idiopathic syndromes comprising a recurring headache disorder, manifesting in attacks lasting 4-72 hours, in which headaches are typically unilateral, throbbing, of moderate to severe intensity, aggravated by routine physical activity, and accompanied by nausea and intolerance to brightness and noise.

TABLE 1

International Headache Society Diagnostic Criteria For Migraine Without Aura

| | |
|---|---|
| A. | At least 5 attacks that fulfill criteria in B, C, D, and E |
| B. | Headache attacks that last 4 to 72 hrs (untreated or unsuccessfully treated) |
| C. | Headache has at least 2 of the following characteristics: Unilateral site Pulsating quality Moderate to severe intensity Aggravation by walking stairs or similar routine physical activity |
| D. | During headache, at least 1 of the following symptoms: Nausea or vomiting (or both) Photophobia and phonophobia No evidence of related organic disease |

Similarly, the International Headache Society provides a set of diagnositic criteria for migraine with aura. These diagnostic criteria are shown in Table 2.

TABLE 2

International Headache Society Criteria For Migraine With Aura

| | |
|---|---|
| A. | At least 2 attacks that fulfill criteria in B and C |
| B. | At least 3 of the following 4 characteristics: |

TABLE 2-continued

International Headache Society Criteria For Migraine With Aura

| | |
|---|---|
| | One or more completely reversible aura symptoms that indicate focal cerebral cortical or brain-stem dysfunction (or both) |
| | At least one aura symptom develops gradually over more than 4 min or two or more symptoms occur in succession |
| | No aura symptom lasts more than 60 min |
| | Headache follows aura in less than 1 hr |
| C. | No evidence of related organic disease |

Most migraines seen in physicians' offices are migraine without aura (formerly called "common migraine") and migraine with aura (formerly called "classic migraine"). Migraine aura without headache is also quite common, and is seen often by ophthalmologists. Neurologists and headache specialists often treat status migrainosus, characterized by a headache phase of over 72 hours. The other migraine types are fully described in *The International Classification of Headache Disorders*, $2^{nd}$ edition, supra.

Not every migraine needs to meet all of the migraine criteria. For example, a person may have a left-temporal throbbing headache of moderate intensity worsened by physical activity. These headache features meet migraine criteria. However, this headache may not be accompanied by nausea or hypersensitivity to light or noise and, therefore, does not fulfill all the criteria for migraine. Yet, if some of this person's other headaches meet all the migraine criteria, then one can say that this headache is also a migraine.

A meticulous history is helpful in assessing and diagnosing any migraine patient. Useful information regarding the history of a subject patient's headache might include, but would not be limited to: age of onset; family history; site or sites of pain; duration; character; intensity; mode of onset; time between onset to peak pain; temporal profile; aggravating or precipitating factors; alleviating factors; associated neurologic, ophthalmologic and autonomic features; prior and current medication use, caffeine use; history of head trauma; results of prior neuroimaging studies; a complete review of systems; or why the patient is currently seeking medical attention.

III. General Laboratory Procedures

When practicing the methods of the invention, a number of general laboratory tests can be used to assist in the diagnosis, progress and prognosis of the patient with migraine, including monitoring of parameters such as blood cortisol, drug metabolism, brain structure and function and the like. These procedures can be helpful because all patients metabolize and react to drugs uniquely. In addition, such monitoring may be important because each GR antagonist has different pharmacokinetics. Different patients and disease conditions may require different dosage regimens and formulations. Such procedures and means to determine dosage regimens and formulations are well described in the scientific and patent literature. A few illustrative examples are set forth below.

a. Determining Blood Cortisol Levels

The invention may be practiced upon patients with apparently normal levels of blood cortisol. However, since the treatment for migraine comprises administration of a glucocorticoid receptor antagonist, monitoring blood cortisol and determining baseline cortisol levels are useful laboratory tests to aid in the diagnosis, treatment and prognosis of a migraine patient. A wide variety of laboratory tests exist that can be used to determine whether an individual is normal, hypo- or hypercortisolemic. Migraine patients typically have normal levels of cortisol that are often less than 25 µg/dl in the morning, and frequently about 15 µg/dl or less in the afternoon, although the values often fall at the high end of the normal range, which is generally considered to be 5-15 µg/dl in the afternoon.

Immunoassays such as radioimmunoassays are commonly used because they are accurate, easy to do and relatively cheap. Because levels of circulating cortisol are an indicator of adrenocortical function, a variety of stimulation and suppression tests, such as ACTH Stimulation, ACTH Reserve, or dexamethasone suppression (see, e.g., Greenwald, *Am. J. Psychiatry* 143:442-446, 1986), can also provide diagnostic, prognostic or other information to be used adjunctively in the methods of the invention.

One such assay available in kit form is the radioimmunoassay available as "Double Antibody Cortisol Kit" (Diagnostic Products Corporation, Los Angeles, Calif.), (*Acta Psychiatr. Scand.* 70:239-247, 1984). This test is a competitive radioimmunoassay in which $^{125}$I-labeled cortisol competes with cortisol from an clinical sample for antibody sites. In this test, due to the specificity of the antibody and lack of any significant protein effect, serum and plasma samples require neither preextraction nor predilution. This assay is described in further detail in Example 2, below.

b. Determination of Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to treat migraine, an illustrative example of determining blood and urine mifepristone levels is set forth in the Example below.

c. Other Laboratory Procedures

Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai *Pharmacol. and Experimental Therapeutics* 241:401-406, 1987.

IV. Glucocorticoid Receptor Antagonists to Treat Migraine in a Subject

The invention provides for methods for treating migraine a subject utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

A. Steroidal Anti-Glucocorticoids as GR Antagonists.

Steroidal glucocorticoid antagonists are administered to treat migraine in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, *J. Steroid Biochem.* 33:557-563, 1989).

Examples of steroidal GR antagonists include androgen-type steroid compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127, and 6,303,591. Such steroidal GR antagonists include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and 17β-hydroxy-17α-19-(4-methylphenyl)androsta-4,9(11)-dien-3-one (RU044).

Other examples of steroidal antiglucocorticoids are disclosed in Van Kampen et al. (2002) Eur. J. Pharmacol. 457(2-3):207, WO 03/043640, EP 0 683 172 B1, and EP 0 763 541 B1, each of which is incorporated herein by reference. EP 0 763 541 B1 and Hoyberg et al., Int'l J. of Neuro-psychopharmacology, 5: Supp. 1, S148 (2002); disclose the compound (11β,17β)-11-(1,3-benzodioxol-5-yl)-17-hydroxy-17-(1-propynyl)estra-4,9-dien-3-one (ORG 34517) which in one embodiment, is administered in an amount effective to treat migraine in a subject.

1. Removal or Substitution of the 11-beta Hydroxy Group

Glucocorticoid antagonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. supra). Preferred embodiments of the invention include all 11-beta-aryl steroid backbone derivatives because these compounds are devoid of progesterone receptor (PR) binding activity (Agarwal, FEBS 217:221-226, 1987). Another preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethyl-aminophenyl)17-alpha-(1-propynyl)estra-4,9-dien-3-one). Mifepristone has been shown to be a powerful antagonist of both the progesterone and glucocorticoid (GR) receptors. Another 11-beta phenyl-aminodimethyl steroids shown to have GR antagonist effects includes RU009 (RU39.009), 11-beta-(4-dimethyl-aminoethoxyphenyl)-17-alpha-(propynyl-17 beta-hydroxy-4,9-estradien-3-one) (see Bocquel, J. Steroid Biochem. Molec. Biol. 45:205-215, 1993). Another GR antagonist related to RU486 is RU044 (RU43.044) 17-beta-hydrox-17-alpha-19-(4-methyl-phenyl)-androsta-4,9 (11)-dien-3-one) (Bocquel, 1993, supra). See also Teutsch, Steroids 38:651-665, 1981; U.S. Pat. Nos. 4,386,085 and 4,912,097.

One embodiment includes compositions containing the basic glucocorticoid steroid structure which are irreversible anti-glucocorticoids. Such compounds include alpha-keto-methanesulfonate derivatives of cortisol, including cortisol-21-mesylate (4-pregnene-11-beta,17-alpha,21-triol-3,20-di-one-21-methane-sulfonate and dexamethasone-21-mesylate (16-methyl-9 alpha-fluoro-1,4-pregnadiene-11 beta,17-alpha,21-triol-3,20-dione-21-methane-sulfonate). See Simons, J. Steroid Biochem. 24:25-32, 1986; Mercier, J. Steroid Biochem. 25:11-20, 1986; U.S. Pat. No. 4,296,206.

2. Modification of the 17-beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17,21-acetonide derivatives and 17-beta-carboxamide derivatives of dexamethasone (Lefebvre, 1989, supra; Rousseau, Nature 279:158-160, 1979).

3. Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoid activity in comparison to 17-propinyl side chain containing compounds.

Additional glucocorticoid receptor antagonists known in the art and suitable for practice of the invention include 21-hydroxy-6,19-oxidoprogesterone (see Vicent, Mol. Pharm. 52:749-753, 1997), Org31710 (see Mizutani, J Steroid Biochem Mol Biol 42(7):695-704, 1992), RU43044, RU40555 (see Kim, J Steroid Biochem Mol Biol. 67(3):213-22, 1998), RU28362, and ZK98299.

B. Non-Steroidal Anti-Glucocorticoids as Antagonists.

Non-steroidal glucocorticoid antagonists are also used in the methods of the invention to migraine in a subject. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour, Int. J. Pept. Protein Res. 43:297-304, 1994; de Bont, Bioorganic & Medicinal Chem. 4:667-672, 1996). The creation and simultaneous screening of large libraries of synthetic molecules can be carried out using well-known techniques in combinatorial chemistry, for example, see van Breemen, Anal Chem 69:2159-2164, 1997; and Lam, Anticancer Drug Des 12:145-167, 1997. Design of peptidomimetics specific for GR can be designed using computer programs in conjunction with combinatorial chemistry (combinatorial library) screening approaches (Murray, J. of Computer-Aided Molec. Design 9:381-395, 1995; Bohm, J. of Computer-Aided Molec. Design 10:265-272, 1996). Such "rational drug design" can help develop peptide isomerics and conformers including cycloisomers, retro-inverso isomers, retro isomers and the like (as discussed in Chorev, TibTech 13:438-445, 1995).

Examples of non-steroidal GR antagonists include keto-conazole, clotrimazole; N-(triphenylmethyl)imidazole; N-([2-fluoro-9-phenyl]fluorenyl)imidazole; N-([2-pyridyl] diphenylmethyl)imidazole; N-(2-[4,4',4"-trichlorotrityl]oxyethyl)morpholine; 1-(2[4,4',4"-trichlorotrityl]oxyethyl)-4-

(2-hydroxyethyl)piperazine dimaleate; N-([4,4',4"]-trichlorotrityl)imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl) benzhydrol; 5-(5-methoxy-2-(N-methylcarbamoyl)-phenyl) dibenzosuberol; N-(2-chlorotrityl)-L-prolinol acetate; 1-(2-chlorotrityl)-2-methylimidazole; 1-(2-chlorotrityl)-1,2,4-triazole; 1,S-bis(4,4',4"-trichlorotrityl)-1,2,4-triazole-3-thiol; and N-((2,6-dichloro-3-methylphenyl)diphenyl) methylimidazole (see U.S. Pat. No. 6,051,573); the GR antagonist compounds disclosed in U.S. Pat. Nos. 5,696,127 and 6,570.020; the GR antagonist compounds disclosed in U.S. patent application No. 20020077356, the glucocorticoid receptor antagonists disclosed in Bradley et al., *J. Med. Chem.* 45, 2417-2424 (2002), e.g., 4α(S)-Benzyl-2(R)-chloroethynyl-1,2,3,4,4α,9,10,10α(R)-octahydro-phenanthrene-2,7-diol ("CP394531") and 4α(S)-Benzyl-2(R)-prop-1-ynyl-1,2,3,4,4α,9,10,10α(R)-octahydro-phenanthrene-2,7-diol ("CP 409069") the compounds disclosed in PCT International Application No. WO 96/19458, which describes non-steroidal compounds which are high-affinity, highly selective antagonists for steroid receptors, such as 6-substituted-1,2-dihydro-N-protected-quinolines; and some κ opioid ligands, such as the κ opioid compounds dynorphin-1,13-diamide, U50,488 (trans-(1R,2R)-3,4-dichloro-N-methyl-N-[2-(1-pyrrolidinyl)cyclohexyl]benzeneacetamide), bremazocine and ethylketocyclazocine; and the non-specific opioid receptor ligand, naloxone, as disclosed in Evans et al., *Endocrin.*, 141:2294-2300 (2000).

C. Identifying Specific Glucocorticoid Receptor Antagonists

Because any specific GR antagonist can be used to treat migraine in a subject, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner, Meth. Enzymol. 15:633, 1970. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p-hydroxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany, Biochem. Biophys. Acta 886:162-168, 1986).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of 3H-thymidine into DNA in cells which are stimulated by glucocorticoids can be used. Alternatively, the putative GR antagonist can complete with 3H-dexamethasone for binding to a hepatoma tissue culture GR (see, e.g., Choi, et al., Steroids 57:313-318, 1992). As another example, the ability of a putative GR antagonist to block nuclear binding of 3H-dexamethasone-GR complex can be used (Alexandrova et al., J. Steroid Biochem. Mol. Biol. 41:723-725, 1992). To further identify putative GR antagonists, kinetic assays able to discriminate between glucocorticoid agonists and antagonists by means of receptor-binding kinetics can also be used (as described in Jones, Biochem J. 204:721-729, 1982).

In another illustrative example, the assay described by Daune, Molec. Pharm. 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR antagonist) at varying concentrations. 3H-uridine is added to the cell culture, which is further incubated, and the extent of incorporation of radiolabel into polynucleotide is measured. Glucocorticoid agonists decrease the amount of 3H-uridine incorporated. Thus, a GR antagonist will oppose this effect.

For additional compounds that can be utilized in the methods of the invention and methods of identifying and making such compounds, see U.S. Pat. Nos. 4,296,206 (see above); 4,386,085 (see above); 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

The specificity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either direct binding assay or by assessing competitive binding to the purified GR or MR in the presence of a known antagonist. In an exemplary assay, cells that are stably expressing the glucocorticoid receptor or mineralocorticoid receptor (see, e.g., U.S. Pat. No. 5,606,021) at high levels are used as a source of purified receptor. The affinity of the antagonist for the receptor is then directly measured. Those antagonists that exhibit at least a 100-fold higher affinity, often 1000-fold, for the GR relative to the MR are then selected for use in the methods of the invention.

A GR-specific antagonist may also be defined as a compound that has the ability to inhibit GR-mediated activities, but not MR-mediated activities. One method of identifying such a GR-specific antagonist is to assess the ability of an antagonist to prevent activation of reporter constructs using transfection assays (see, e.g., Bocquel et al, J. Steroid Biochem Molec. Biol. 45:205-215, 1993; U.S. Pat. Nos. 5,606, 021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. A GR-specific antagonist is considered to exhibit at least a 100-fold, often 1000-fold or greater, activity towards the GR relative to the MR.

V Treating Migraine in a Subject Using Glucocorticoid Receptor Antagonists

Antiglucocorticoids, such as mifepristone, are formulated as pharmaceuticals to be used in the methods of the invention to treat migraine in a subject. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

A. Glucocorticoid Receptor Antagonists as Pharmaceutical Compositions

The GR antagonists used in the methods of the invention can be administered by any means known in the art, e.g., parenterally, topically, orally, or by local administration, such as by aerosol or transdermally. The methods of the invention provide for prophylactic and/or therapeutic treatments. The GR antagonists as pharmaceutical formulations can be administered in a variety of unit dosage forms depending upon whether the migraine is being treated during an attack, or prophylactically, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's"). Therapeutically effective amounts of glucocorticoid blockers suitable for practice of the method of the invention will typically range from about 0.5 to about 35 milligrams per kilogram (mg/kg). A person of ordinary skill in the art will be able without undue experimentation, having regard to that skill and this disclosure, to determine a therapeutically effective amount of a particular glucocorticoid blocker compound for practice of this invention. For example, a particular glucocorticoid blocker may be more effective at higher or lower doses. By evaluating a patient using the methods described herein, a skilled practitioner will be able to determine whether a patient is responding to treatment and will know how to adjust the dosage levels accordingly.

In general, glucocorticoid blocker compounds may be administered as pharmaceutical compositions by any method known in the art for administering therapeutic drugs. Compositions may take the form of tablets, pills, capsules, semi-solids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Glucocorticoid blocker pharmaceutical formulations can be prepared according to any method known to the art for the manufacture of pharmaceuticals. Such drugs can contain sweetening agents, flavoring agents, coloring agents and preserving agents. Any glucocorticoid blocker formulation can be admixtured with nontoxic pharmaceutically acceptable excipients which are suitable for manufacture.

In one aspect, glucocorticoid blocker compounds suitable for use in the practice of this invention can be administered orally. The amount of a compound of this invention in the composition may vary widely depending on the type of composition, size of a unit dosage, kind of excipients, and other factors well known to those of ordinary skill in the art. In general, the final composition may comprise from 0.000001 percent by weight (% w) to 10% w of the glucocorticoid blocker compounds, preferably 0.00001% w to 1% w, with the remainder being the excipient or excipients. For example, the GR antagonist mifepristone is given orally in tablet form, with dosages in the range of between about 0.5 and 35 mg/kg, in other embodiments, dosages may range between about 0.75 mg/kg and 15 mg/kg, or may be about 10 mg/kg.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Pharmaceutical preparations for oral use can be obtained through combination of glucocorticoid blocker compounds with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

In another aspect, the GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

In another aspect, the GR antagonists of this invention can be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

In another aspect, the GR antagonists of the invention can also be delivered transdermally, by a topical route, formulated as applicator sticks, solutions, suspensions, emulsions, gels, creams, ointments, pastes, jellies, paints, powders, and aerosols.

In still another aspect, the GR antagonists of the invention can also be delivered as microspheres for slow release in the body. For example, microspheres can be administered via intradermal injection of drug (e.g., mifepristone)-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use.

In one embodiment, the GR antagonist formulations of the invention are useful for parenteral administration, such as intravenous (IV) administration. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

B. Determining Dosing Regimens for Glucocorticoid Receptor Antagonists

The methods of this invention treat migraine in a subject. The amount of GR antagonist adequate to accomplish this is defined as a "therapeutically effective dose". The dosage schedule and amounts effective for this use, i.e., the "dosing regimen," will depend upon a variety of factors, including the severity of the migraine, whether the treatment is being given during the course of a migraine attack, or prophylactically, the patient's physical status, age, migraine history, and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones, J. Steroid Biochem. Mol. Biol. 58:611-617, 1996; Groning, Pharmazie 51:337-341, 1996; Fotherby, Contraception 54:59-69, 1996; Johnson, J. Pharm. Sci. 84:1144-1146, 1995; Rohatagi, Pharmazie 50:610-613, 1995; Brophy, Eur. J. Clin. Pharmacol. 24:103-108, 1983; the latest Remington's, supra). For example, in one study, less than 0.5% of the daily dose of mifepristone was excreted in the urine; the drug bound extensively to circulating albumin (see Kawai, supra, 1989). The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively treat migraine in a subject. Thus, one typical pharmaceutical formulations for oral administration of mifepristone is in a daily amount of between about 0.5 to about 35 mg per kilogram of body weight per day. In an alternative embodiment, dosages are from about 5 mg to about 15 mg per kg of body weight per patient per day are used in the practice of the invention. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as et al., eds., De Gruyter, New York, 1987.

After a pharmaceutical comprising a GR antagonist of the invention has been formulated in a acceptable carrier, it can be placed in an appropriate container and labeled for treatment of an indicated condition. For administration of GR antagonists, such labeling would include, e.g., instructions concerning the amount, frequency and method of administration. In one embodiment, the invention provides for a kit for treating migraine in a subject which includes a GR antagonist and instructional material teaching the indications, dosage and schedule of administration of the GR antagonist.

It is understood that the examples and embodiments described herein are for illustrative purposes only and that various modifications or changes in light thereof will be suggested to persons skilled in the art and are to be included within the spirit and purview of this application and scope of the appended claims.

All publications and patent applications cited in this specification are herein incorporated by reference as if each individual publication or patent application were specifically and individually indicated to be incorporated by reference.

EXAMPLES

The following examples are offered to illustrate, but not to limit the claimed invention.

Example 1

Treating Migraine Prophylactically Using Mifepristone

A person presents with migraine symptoms including: 10 migraine headache attacks that last 4 to 72 hrs and are not yet successfully treated, the headaches have a pulsating quality, and are aggravated by walking stairs. During the headaches, the subject experiences nausea and vomiting and is completely incapacitated and unable to cope. The migraines typically occur two or more times per month, but there is no evidence of related organic disease.

The subject will have a diagnosis of migraine without aura. The diagnosis is made in accordance with the criteria set forth in: *The International Classification of Headache Disorders*, $2^{nd}$ edition, Headache Classification Committee of the International Headache Society, supra.

Treatment with the glucocorticoid receptor (GR) antagonist, mifepristone (available from commercial sources such as Shanghai HuaLian Pharmaceuticals Co., Ltd., Shanghai, China), is initiated. Since the migraines occur frequently, last more than 48 hours, and the subject finds the attacks intolerable, prophylactic treatment is initiated.

The subject is instructed to take a dosage of 600 mg daily, and to continue the mifepristone daily for six months. Dosages will be adjusted if necessary and further evaluations will be performed periodically throughout treatment.

Assessing Pain Reduction:

To delineate and assess the effectiveness of mifepristone in treating the subject's migraine, the frequency of migraine attacks, their severity and their accompanying symptoms are recorded and measured at baseline, 3 months, and 6 months.

Example 2

Measuring Cortisol Levels

To measure cortisol level in the subject of Example 1, afternoon Cortisol Test measurements are taken and used as the baseline cortisol measure. Cortisol levels are taken at Day 0, at two weeks after receiving the medication (Day 14), and each visit for up to six months and periodically thereafter.

The "Double Antibody Cortisol Kit" (Diagnostic Products Corporation, Los Angeles, Calif.) is used to measure blood cortisol levels. This test is a competitive radioimmunoassay in which $^{125}$I-labeled cortisol competes with cortisol from an clinical sample for antibody sites, and is performed essentially according to manufacturer's instructions using reagents supplied by manufacturer. Briefly, blood is collected by venipuncture and serum separated from the cells. The samples are stored at 2 to 8° C. for up to seven days, or up to two month frozen at −20° C. Before the assay, samples are allowed to come up to room temperature (15-28° C.) by gentle swirling or inversion. Sixteen tubes in duplicate at 25 microliters of serum per tube are prepared. Cortisol concentrations are calculated from the prepared calibration tubes. Net counts equal the average CPM minus the average non-specific CPM. Cortisol concentrations for the unknowns are estimated by interpolation from the calibration curve (Dudley et al., Clin. Chem. 31: 1264-1271, 1985).

Example 3

Treating Migraine Acutely Using Mifepristone

A person presents with migraine symptoms including: 10 migraine headache attacks that last 4 to 72 hrs and are not yet successfully treated, the headaches have a pulsating quality, and are aggravated by walking stairs. During the headaches, the subject experiences nausea and vomiting, but manages to cope. The migraines typically occur two or three times per year, and there is no evidence of related organic disease.

The subject will have a diagnosis of migraine without aura. The diagnosis is made in accordance with the criteria set forth in: *The International Classification of Headache Disorders*, $2^{nd}$ edition, Headache Classification Committee of the International Headache Society, supra.

Treatment with the glucocorticoid receptor (GR) antagonist, mifepristone is initiated. Since the migraines occur infrequently, and the subject can cope with the attacks acute treatment is initiated.

The subject is instructed to take a dosage of 600 mg at the first sign or symptom of migraine. The subject is further instructed to take notes regarding the quality and severity of any migraine attacks. The subject will return for an assessment of mifepristone treatment at six month intervals for a period of two years. Dosages will be adjusted if necessary throughout treatment.

It is understood that the examples and embodiments described herein are for illustrative purposes only and that various modifications or changes in light thereof will be suggested to persons skilled in the art and are to be included within the spirit and purview of this application and scope of the claims.

What is claimed is:

1. A method of treating migraine in a subject in need thereof, the method comprising the step of administering to the subject an amount of a specific glucocorticoid receptor antagonist effective to treat migraine in the subject wherein the glucocorticoid receptor antagonist is a nonsteroidal glucocorticoid receptor antagonist with the proviso that the subject is not otherwise in need of treatment with a glucocorticoid receptor antagonist.

2. The method of claim 1, wherein the glucocorticoid receptor antagonist is selected from the group consisting 4α(S)-Benzyl-2(R)-prop-1-ynyl-1,2,3,4,4α,9,10,10α(R)-octahydro-phenanthrene-2,7-diol and 4α(S)-Benzyl-2(R)-chloroethynyl-1,2,3,4,4α,9,10,10α(R)-octahydro-phenanthrene-2,7-diol.

3. The method of claim 1, wherein the treatment for migraine is administered during the course of a migraine attack.

4. The method of claim 1, wherein the glucocorticoid receptor antagonist is administered in a daily amount of between about 0.5 to about 35 mg per kilogram of body weight per day.

5. The method of claim 1, wherein the glucocorticoid receptor antagonist is administered in a daily amount of between about 5 to about 15 mg per kilogram of body weight per day.

6. The method of claim 1, wherein the administration is once per day.

7. The method of claim 1, wherein the mode of administration is by a transdermal application, by a nebulized suspension, or by an aerosol spray.

8. The method of claim 1, wherein the mode of administration is oral.

* * * * *

UNITED STATES PATENT AND TRADEMARK OFFICE
CERTIFICATE OF CORRECTION

| | | |
|---|---|---|
| PATENT NO. | : 8,450,379 B2 | Page 1 of 1 |
| APPLICATION NO. | : 10/703069 | |
| DATED | : May 28, 2013 | |
| INVENTOR(S) | : Belanoff | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1153 days.

Signed and Sealed this
Thirtieth Day of December, 2014

Michelle K. Lee
*Deputy Director of the United States Patent and Trademark Office*